(12) United States Patent
Chang

(10) Patent No.: US 12,259,452 B2
(45) Date of Patent: Mar. 25, 2025

(54) DYNAMIC SHIMMING FOR ARTERIAL SPIN LABELING

(71) Applicant: Siemens Healthineers AG, Forchheim (DE)

(72) Inventor: Yulin Chang, Belmont, MA (US)

(73) Assignee: Siemens Healthineers AG, Forchheim (DE)

(*) Notice: Subject to any disclaimer, the term of this patent is extended or adjusted under 35 U.S.C. 154(b) by 163 days.

(21) Appl. No.: 18/311,373

(22) Filed: May 3, 2023

(65) Prior Publication Data

US 2024/0369660 A1 Nov. 7, 2024

(51) Int. Cl.
- *G01R 33/54* (2006.01)
- *A61B 5/026* (2006.01)
- *G01R 33/56* (2006.01)
- *G01R 33/565* (2006.01)

(52) U.S. Cl.
CPC .......... *G01R 33/543* (2013.01); *A61B 5/0263* (2013.01); *G01R 33/5608* (2013.01); *G01R 33/56563* (2013.01)

(58) Field of Classification Search
CPC .............. G01R 33/543; G01R 33/5608; G01R 33/56563; A61B 5/0263; A61B 5/055; A61B 5/743
See application file for complete search history.

(56) References Cited

U.S. PATENT DOCUMENTS

| 9,606,205 B1 * | 3/2017 | Ito ................... G01R 33/56366 |
| 2015/0305645 A1 * | 10/2015 | Ouyang ................. A61B 5/145 600/419 |
| 2022/0304582 A1 * | 9/2022 | Chang ................. A61B 5/0263 |

OTHER PUBLICATIONS

Detre, John A., et al. "Perfusion imaging." Magnetic resonance in medicine 23.1 (1992): 37-45.
Buxton, Richard B. "Quantifying CBF with arterial spin labeling." Journal of Magnetic Resonance Imaging: An Official Journal of the International Society for Magnetic Resonance in Medicine 22.6 (2005): 723-726.
Aguirre, Geoffrey Karl, et al. "Experimental design and the relative sensitivity of BOLD and perfusion fMRI." Neuroimage 15.3 (2002): 488-500.
Alsop, David C., et al. "Arterial spin labeling blood flow MRI: its role in the early characterization of Alzheimer's disease." Journal of Alzheimer's Disease 20.3 (2010): 871-880.
(Continued)

*Primary Examiner* — G. M. A Hyder

(57) ABSTRACT

Systems and methods include determination of first shim channels and respective first shim currents to label a labeling region and image an imaging volume, determination of second shim channels and respective second shim currents to label the labeling region, and respective third shim currents to image the imaging volume, execution of a labeling phase of a pulse sequence while the first shim currents are applied to the first shim channels and the second shim currents are applied to the second shim channels, execution of a readout phase of the pulse sequence to readout signals from the imaging volume while the third shim currents are applied to the second shim channels and the first shim currents are applied to the first shim channels, and generation of an image based on the signals.

20 Claims, 5 Drawing Sheets

(56) References Cited

OTHER PUBLICATIONS

Kim, Seong-Gi. "Quantification of relative cerebral blood flow change by flow-sensitive alternating inversion recovery (FAIR) technique: application to functional mapping." Magnetic resonance in medicine 34.3 (1995): 293-301.

Dai, Weiying, et al. "Continuous flow-driven inversion for arterial spin labeling using pulsed radio frequency and gradient fields." Magnetic Resonance in Medicine: An Official Journal of the International Society for Magnetic Resonance in Medicine 60.6 (2008): 1488-1497.

Jahanian, Hesamoddin, Douglas C. Noll, and Luis Hernandez-Garcia. "B0 field inhomogeneity considerations in pseudo-continuous arterial spin labeling (pCASL): effects on tagging efficiency and correction strategy." NMR in Biomedicine 24.10 (2011): 1202-1209.

Luh, Wen-Ming, et al. "Pseudo-continuous arterial spin labeling at 7 T for human brain: estimation and correction for off-resonance effects using a Prescan." Magnetic Resonance in Medicine 69.2 (2013): 402-410.

Saib, Gael, Alan Koretsky, and S. Lalith Talagala. "PCASL labeling efficiency measurement with B0 off-resonance compensation at 7T", ISMRM 2021;2726.

Jung, Youngkyoo, Eric C. Wong, and Thomas T. Liu. "Multiphase pseudocontinuous arterial spin labeling (MP-PCASL) for robust quantification of cerebral blood flow." Magnetic resonance in medicine 64.3 (2010): 799-810.

Shin, David D., et al. "Pseudocontinuous arterial spin labeling with optimized tagging efficiency." Magnetic resonance in medicine 68.4 (2012): 1135-1144.

Zhao, Li, et al. "Improving the robustness of pseudo-continuous arterial spin labeling to off-resonance and pulsatile low velocity." Magnetic resonance in medicine 78.4 (2017): 1342-1351.

Berry, Eleanor SK, Peter Jezzard, and Thomas W. Okell. "Off-resonance correction for pseudo-continuous arterial spin labeling using the optimized encoding scheme." NeuroImage 199 (2019): 304-312.

Guterres, Sofia, et al. "Brain perfusion imaging using pseudo-continuous arterial spin labelling MRI: impact of RF coil shimming of the labelling region", ISMRM & SMRT Annual Meeting & Exhibition, May 15-20, 2021, 3 pages.

Kim, Tae, et al. "Gradient-echo EPI using a high-degree shim insert coil at 7 T: Implications for BOLD f MRI." Magnetic resonance in medicine 78.5 (2017): 1734-1745.

\* cited by examiner

DYNAMIC SHIMMING FOR ARTERIAL SPIN LABELING

BACKGROUND

Magnetic Resonance (MR) imaging uses magnetic fields and radio-frequency (RF) pulses to non-invasively image the organs, tissues and the physiological processes of the body. Arterial spin labeling (ASL) is a particular MR imaging technique for evaluating blood perfusion. According to ASL, water nuclei in the blood are magnetically labeled before the blood perfuses into tissue, and k-space signals are acquired from the tissue while the magnetically-labeled blood is present in the tissue. Images are generated based on the k-space signals and blood perfusion within the tissue may be evaluated therefrom.

Several types of ASL techniques exist. In pulsed ASL (PASL), blood surrounding the imaging volume is labeled using a single pulse which defines the volume of arterial blood to be labeled. In continuous ASL (CASL) and pseudo-continuous ASL (pCASL), blood located upstream of the imaging volume is continuously inverted or saturated as it passes a particular plane.

pCASL uses a narrow labeling plane through which a long train of short, Hanning-windowed block RF pulses causes flow-related adiabatic inversion of arterial spins. The labeling plane is usually located immediately proximal to the imaging volume, which minimizes signal loss from the decay of the thusly-labeled blood. pCASL is the most widely used ASL implementation because it affords high labeling efficiency (i.e., Signal-to-Noise Ratio).

Since excitation RF pulses are applied to both the labeling region and the imaging volume, ASL is susceptible to inhomogeneity of the $B_0$ magnetic field in the labeling region as well as in the imaging volume. Inhomogeneity of the $B_0$ magnetic field within the imaging volume may cause image artifacts such as blurring, signal dropout, and geometric distortion. Similarly, $B_0$ inhomogeneity or off-resonance in the labeling plane can significantly reduce the labeling efficiency.

The presence of off-resonant $B_0$ fields is particularly common in pCASL because the MR scanner shim is typically calculated to prioritize maintaining $B_0$ field homogencity of the imaging volume over that of the labeling plane. As a result, the labeling plane is usually left unshimmed, leading to inconsistent $B_0$ off-resonance in the labeling region. The $B_0$ off-resonance in the labeling plane can be exacerbated by any shimming of the imaging volume which leads to unwanted magnetic field changes in the labeling plane. $B_0$ off-resonance in the labeling plane can also be caused by the presence of magnetic materials near the labeling plane such as dental implants. If left unaddressed, $B_0$ off-resonance in the labeling plane will result in varying labeling efficiencies between subjects and between scans, and ultimately result in inconsistent and incorrect blood perfusion measurement.

Prior attempts to address the foregoing include a calibration scan for off-resonance in the labeling plane or adding a phase factor to the labeling RF pulse, independently or in combination with the optimization of the gradient pulses, to improve labeling efficiency. Recently, a method was proposed that attempts to optimize $B_1$ and gradient fields in unbalanced pCASL (ubpCASL) to improve the labeling efficiency for off-resonance blood. None of these methods directly addresses the underlying problem of $B_0$ field off-resonance at the labeling plane.

Systems to efficiently achieve $B_0$ resonance in the labeling plane and in the imaging volume during ASL imaging are desired.

DETAILED DESCRIPTION

The following description is provided to enable any person in the art to make and use the described embodiments. Various modifications, however, will remain readily apparent to those in the art.

For purposes of the present description, a shim channel will refer to hardware through which direct current (i.e., a shim current) flows in order to alter a surrounding magnetic field. A shim channel is considered "off" if no current is flowing therethrough (in which case the shim channel does not alter the surrounding magnetic field). The effect of a shim channel on the magnetic field depends in part on the magnitude of the direct current flowing therethrough. In MR imaging, the magnitude of the shim current is selected in order to produce a desired effect (e.g., homogeneity) on the magnetic field. The act of applying a shim current to a shim channel is referred to herein as "shimming".

A shim channel typically consists of metal wound into a loop. MR imaging may utilize shim channels provided by an MR scanner (i.e., "spherical harmonics"-1st order (linear), 2nd order, 3rd order, etc.), a shim insert, or a local shim coil. Some of these shim channels can be dynamically switched from carrying one stable shim current to carrying another stable shim current within a short amount of time (e.g., ~1 s). This subset of shim channels will be referred to as "dynamic" shim channels while other shim channels are referred to as "static" shim channels. Examples of dynamic shim channels in some embodiments may include a linear shim of an MR scanner, shim channels of a shim insert, and shim channels of local shim coils.

According to some embodiments, shim currents are applied to static shim channels and to dynamic shim channels to shim a $B_0$ field in a labeling region during a labeling period. After the labeling period, the shim currents applied to one or more of the dynamic shim channels are switched to other shim current values prior to a readout period. Accordingly, during the readout period, the $B_0$ field in the imaging region is shimmed by the static shim channels (and their original shim currents) and the dynamic shim channels (and their new shim currents). Consequently, labeling efficiency can be improved due to a reduction in $B_0$ off-resonance in the labeling plane during labeling, and image quality is maintained by reducing $B_0$ off-resonance in the imaging volume during readout.

Unlike the approaches described above, some embodiments do not require updating the phase of the RF pulse or the gradient strength to address $B_0$ off-resonance in the labeling plane, and thus can be more easily executed in a clinical setting. Some embodiments also do not require separate shim coil arrays near the labeling region, but rather may utilize only shim channels provided by the MR scanner (e.g., 0-order, first order, second order, third order).

Figure 1:
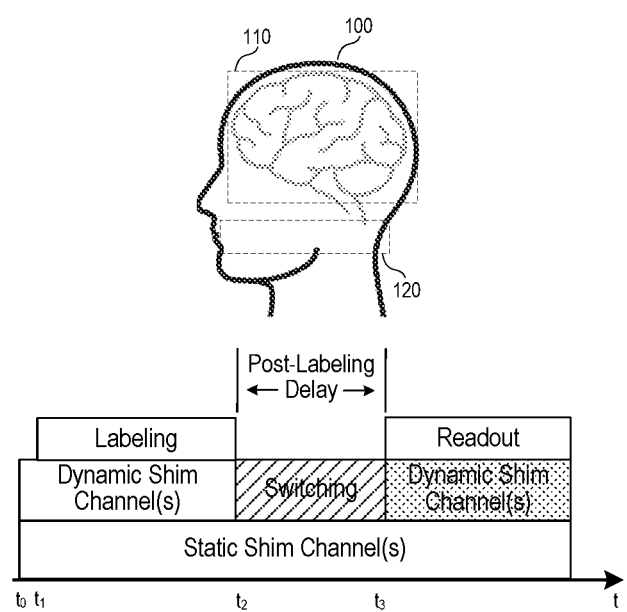
FIG. 1 illustrates dynamic shimming of a labeling region and an imaging volume according to some embodiments.

FIG. 1 illustrates dynamic shimming of a labeling region and an imaging volume according to some embodiments.

It will be assumed that subject 100 of FIG. 1 is disposed within the bore of an MR scanner at time to. Subject 100 is to be subjected to an MR pulse sequence in order to acquire k-space data from imaging volume 110 which includes the brain. Embodiments are not limited to this imaging volume or to a single imaging volume. The example below will describe a pCASL pulse sequence, but embodiments are also not limited thereto.

FIG. 1 also shows labeling region 120, which may comprise a plane or a volume. A location of labeling region 120 is selected to ensure that molecules labeled in that region flow to imaging volume 110 shortly after such labeling. Embodiments are not limited to the location of labeling region 120 or to one labeling region.

Respective shim currents are applied to one or more static shim channels and to one or more dynamic shim channels from time $t_0$ to time $t_2$. The period between time $t_1$ and time $t_2$ may be considered a preparation or labeling phase of a pulse sequence. Accordingly, a labeling phase of the pulse sequence is executed from time $t_1$ to time $t_2$ to label molecules in the labeling region.

The shim channels may comprise any shimming hardware that is or become known. The respective shim currents applied from time $t_1$ to time $t_2$ are pre-determined to reduce $B_0$ off-resonance in labeling region 120 during the labeling phase. One or more of the shim currents may be applied for only a portion of the time period from time $t_1$ to time $t_2$. That is, not all of the shim currents are necessarily applied during the entire time period.

A post-labeling delay elapses between time $t_2$ and time $t_3$. This post-labeling delay is known in the art of pCASL sequences and is intended to allow the now-labeled molecules to flow to imaging volume 110. The post-labeling delay may comprise any suitable length of time. The shim currents applied to the static shim channels remain constant during the post-labeling delay. However, the shim currents applied to one or more of the dynamic shim channels are switched to new shim currents during the post-labeling delay.

It is assumed that any changed shim currents have stabilized within their respective dynamic shim channels by $t_3$. Accordingly, from time $t_3$ to time $t_4$, the original shim currents applied to the static shim channels remain and the dynamic shim channels carry at least one new shim current. The shim currents applied between time $t_3$ and time $t_4$ are intended to reduce $B_0$ off-resonance in imaging volume 110 during this time period. The MR scanner also applies readout pulses suitable to readout signals from imaging volume 110 between time $t_3$ and time $t_4$. The readout pulses may comprise an echo-planar imaging pulse sequence, a fast spin echo pulse sequence, a gradient-recalled echo pulse sequence, or any other suitable pulse sequence.

An image may be generated based on the signals acquired from imaging volume 110 during the readout phase as is known in the art. The image may be compared with an image generated using the same readout pulse sequence and imaging shim(s) but without a preceding labeling phase. For example, a difference between the two images may be calculated to generate a unitless perfusion-weighted image.

Figure 2:
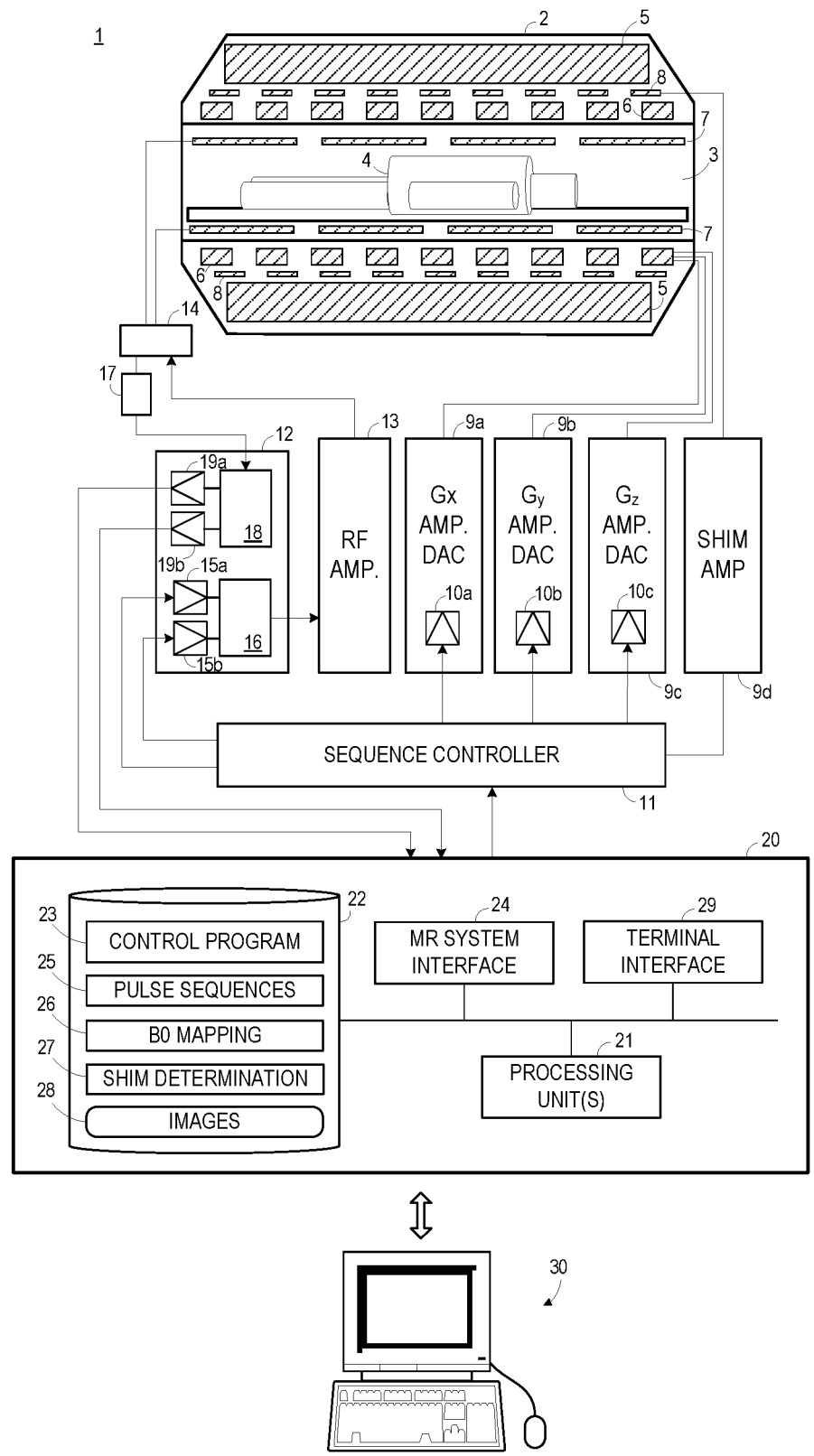
FIG. 2 is a block diagram of an MR imaging system according to some embodiments.

FIG. 2 is a block diagram of MR imaging system 1 for executing pulse sequences to acquire k-space data and reconstructing images therefrom according to some embodiments. Embodiments are not limited to MR system 1.

In MR imaging, a volume of material (e.g., human tissue) is subjected to a main polarizing magnetic field (i.e., $B_0$), causing the individual magnetic moments of the nuclear spins in the substance to process about the polarizing field in random order at their characteristic Larmor frequency, in an attempt to align with the field. A net magnetic moment $M_z$ is produced in the direction of the polarizing field, and the randomly oriented magnetic components in the perpendicular plane (the x-y plane) cancel out one another.

The material is then subjected to an excitation field (i.e., $B_1$) created by emission of a RF pulse, which is in the x-y plane and near the Larmor frequency, causing the net aligned magnetic moment $M_z$ to rotate into the x-y plane so as to produce a net transverse magnetic moment $M_t$, which is rotating, or spinning, in the x-y plane at the Larmor frequency. The excitation field is terminated, and signals are emitted by the excited spins as they return to their pre-excitation field state. The emitted signals (i.e., k-space data) are detected, digitized and processed to reconstruct an image using one of many well-known MR reconstruction techniques.

MR system 1 includes MR chassis 2, which defines bore 3 in which subject 4 is disposed. MR chassis 2 includes polarizing main magnet 5, gradient coils 6 and RF coils 7 arranged about bore 3. According to some embodiments, polarizing main magnet 5 generates a main magnetic field ($B_0$) and RF coils 7 emit an excitation field ($B_1$).

Gradient coils 6 produce magnetic field gradients $G_x$, $G_y$, and $G_z$ which are used for position-encoding MR signals. The magnetic field gradients $G_x$, $G_y$, and $G_z$ distort the main magnetic field in a predictable way so that the Larmor frequency of nuclei within the main magnetic field varies as a function of position. Accordingly, an excitation field $B_1$ which is near a particular Larmor frequency will tip the net aligned moment $M_z$ of those nuclei located at field positions which correspond to the particular Larmor frequency, and signals will be emitted only by those nuclei after the excitation field $B_1$ is terminated.

Gradient coils 6 may consist of three windings, for example, each of which is supplied with current by a respective power amplifier $9a$-$9c$ in order to generate a linear gradient field in its respective Cartesian direction (i.e., x, y, or z). Each amplifier $9a$-$9c$ includes a digital-analog converter $10a$-$10c$ which is controlled by sequence controller 11 to generate desired gradient pulses at proper times.

MR system 1 includes shim coils 8 disposed around bore 3 in between gradient coils 8 and main magnet 5. Embodiments are not limited to this arrangement of shim coils 8. Sequence controller 11 controls shim power amplifier $9d$ to provide desired shim currents to shim coils 8. The shim currents are intended to adjust the $B_0$ field at particular locations (e.g., a labeling region, an imaging volume) to correct for any inhomogeneity and/or off-resonance. Shim power amplifier $9d$ is typically significantly less powerful than power amplifiers $9a$-$9c$ and therefore the shim currents applied to shim coils 8 cannot be switched quickly in a reliable manner.

Shim coils 8 may comprise superconducting and/or resistive shim coils which provide $2^{nd}$-order shimming, $3^{rd}$-order shimming, etc. MR system 1 may also or alternatively provide shimming in some embodiments using a $0^{th}$-order "shim channel" consisting of frequency adjustment and/or a $1^{st}$-order linear shim channel implemented by gradient coils 6. Embodiments may also or alternatively utilize local shim components (e.g., shim coil arrays) placed near or on subject 4 and/or shim inserts inserted into bore 3 (e.g., very high-order shim (VHOS) insert for the brain) as is known in the art.

Local shim components and shim inserts typically exhibit low inductance and therefore may be switched to a stable state and turned off quickly. Accordingly, such components may be considered dynamic shim channels and are particularly suited for dynamic switching during a pulse sequence as described herein. Slower-switching components such as shim coils 8 may be considered static shim channels that are energized with fixed static shim currents during both the labeling and readout phases, with the shim currents applied to the faster-switching dynamic shim channels being dynamically changed between the labeling and readout phases as needed to establish the desired $B_0$ field profiles.

Examples of local shim components include a local cranial/brain shim coil device and a cervical/neck shim coil device. A local cranial/brain shim coil device may comprise a wearable coil device that includes an array of shim coils and a housing body that can be wrapped, molded, placed, worn, or otherwise temporarily affixed to a patient's head such that the coils partially surround the brain while the patient is located in a bore of an MR scanner.

The coils may be integrated into a flexible wrap-around body or rigidly coupled to a helmet body worn by the patient. The coils may include at least a subset of coils that extend below the brain to allow labeling of arterial blood in a labeling region (e.g., in the cervical region). The coils may include an array of 32 seven-turn coils that are arranged three-dimensionally around the patient's brain in close proximity to (or touching) the patient's head when worn.

A cervical/neck shim coil device is also a wearable device that includes an array of shim coils and a body. The body can be constructed similar to a cervical collar stabilization device, allowing the cervical/neck shim coil device to be rigidly affixed to a patient's neck area. Such a device may be worn on the back of the patient's head, making it more comfortable than a stabilization device. The shim coils of a cervical/neck shim coil device may include an array of twelve seven-turn coils that are arranged three-dimensionally around the patient's cervical region in close proximity to (or touching) the patient's neck worn.

Each direct current shim coil in a coil array may be considered a shim channel as described herein. Applying direct current to the coils allows manipulation of the $B_0$ field created by the main MR magnet to improve homogeneity or to improve resonance in desired regions as described herein.

Sequence controller 11 also controls the generation of RF pulses by RF system 12 and RF power amplifier 13. RF system 12 and RF power amplifier 13 are responsive to a scan prescription and direction from sequence controller 11 to produce RF pulses of the desired frequency, phase, and pulse amplitude waveform. The generated RF pulses may be applied to each of RF coils 7. RF coils 7 convert the RF pulses emitted by RF power amplifier 13, via multiplexer 14, into a magnetic alternating field in order to excite the nuclei and align the nuclear spins of the object to be examined or the region of the object to be examined. RF pulses may be emitted in a magnetization preparation step in order to enhance or suppress certain signals.

The RF pulses are represented digitally as complex numbers. Sequence controller 11 supplies these numbers in real and imaginary parts to digital-analog converters 15a-15b in RF system 12 to create corresponding analog pulse sequences. Transmission channel 16 modulates the pulse sequences with a radio-frequency carrier signal having a base frequency corresponding to the resonance frequency of the nuclear spins in the volume to be imaged.

RF coils 7 both emit radio-frequency pulses as described above and scan the alternating field which is produced as a result of processing nuclear spins, i.e., the nuclear spin echo signals. The received signals are received by multiplexer 14, amplified by RF amplifier 17 and demodulated in receiving channel 18 of RF system 12 in a phase-sensitive manner. Analog-digital converters 19a and 19b convert the demodulated signals into real and imaginary components.

Computing system 20 receives the real and imaginary components from analog-digital converters 19a and 19b and may process the components according to known techniques. Such processing may, for example, reconstructing two-dimensional or three-dimensional images by performing a Fourier transformation of k-space data, performing other image reconstruction techniques such as iterative or back-projection reconstruction techniques, applying filters to raw k-space data or to reconstructed images, generating functional magnetic resonance images, calculating motion or flow images, and generating a chemical shift vs. magnitude spectrum.

System 20 may comprise any general-purpose or dedicated computing system. Accordingly, system 20 includes one or more processing units 21 (e.g., processors, processor cores, execution threads, etc.) configured to execute processor-executable program code to cause system 20 to operate as described herein, and storage device 22 for storing the program code. Storage device 22 may comprise one or more fixed disks, solid-state random-access memory, and/or removable media (e.g., a thumb drive) mounted in a corresponding interface (e.g., a USB port).

Storage device 22 stores program code of control program 23. One or more processing units 21 may execute control program 23 to provide instructions to sequence controller 11 via MR system interface 24. For example, sequence controller 11 may be instructed to initiate a desired pulse sequence of pulse sequences 25, such as a pCASL pulse sequence according to some embodiments. In particular, sequence controller 11 may be instructed to control the switching of magnetic field gradients via amplifiers 9a-9d at appropriate times, the transmission of radio-frequency pulses having a specified phase and amplitude at specified times via RF system 12 and RF amplifier 13, and the readout of the resulting MR signals.

Storage device 22 stores program code of $B_0$ mapping component 26 and shim determination component 27. $B_0$ mapping component 26 may implement known algorithms executable to evaluate the $B_0$ field within a given volume of subject 4. Relatedly, shim determination component 27 may comprise program code executable to determine shim currents to apply to shim channels during a labeling phase and a readout phase as described herein. Shim determination component 27 may utilize the output of $B_0$ mapping component 26 to determine shim currents for addressing inhomogeneity/off-resonance in the labeling region during the labeling phase and to determine shim currents for addressing inhomogeneity/off-resonance in the imaging volume during the readout phase.

Images 28 of subject 4 may be generated conventionally and/or as described herein. Images 28 may be provided to terminal 30 via terminal interface 29 of system 20. Terminal interface 29 may also receive input from terminal 30, which may be used to provide commands to control program 23 in order to control sequence controller 11 and/or other elements of system 1. The commands may include commands to specify a labeling region and an imaging volume and commands to initiate a pulse sequence to acquire image data of a subject. Terminal 30 may simply comprise a display device and an input device coupled to system 20. In some embodiments, terminal 30 is a separate computing device such as, but not limited to, a desktop computer, a laptop computer, a tablet computer, and a smartphone.

Each element of system 1 may include other elements which are necessary for the operation thereof, as well as additional elements for providing functions other than those described herein. Storage device 22 may also store data and other program code for providing additional functionality and/or which are necessary for operation of system 20, such as device drivers, operating system files, etc.

Figure 3A:
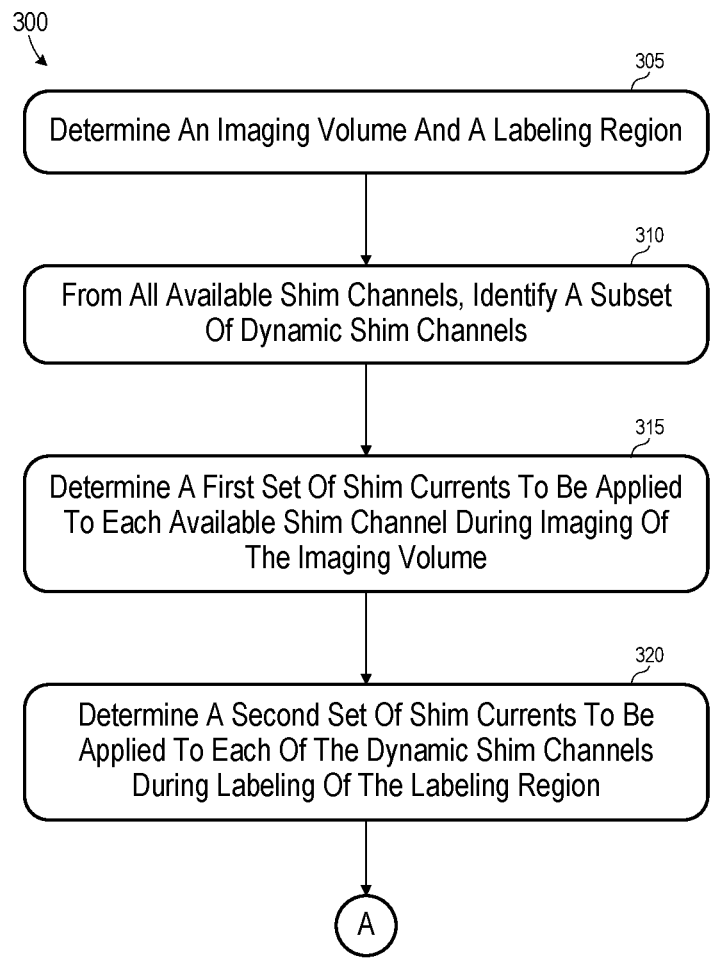
FIGS. 3A and 3B comprise a flow diagram of a process to dynamically shim a labeling region and an imaging volume according to some embodiments.
Figure 3B:
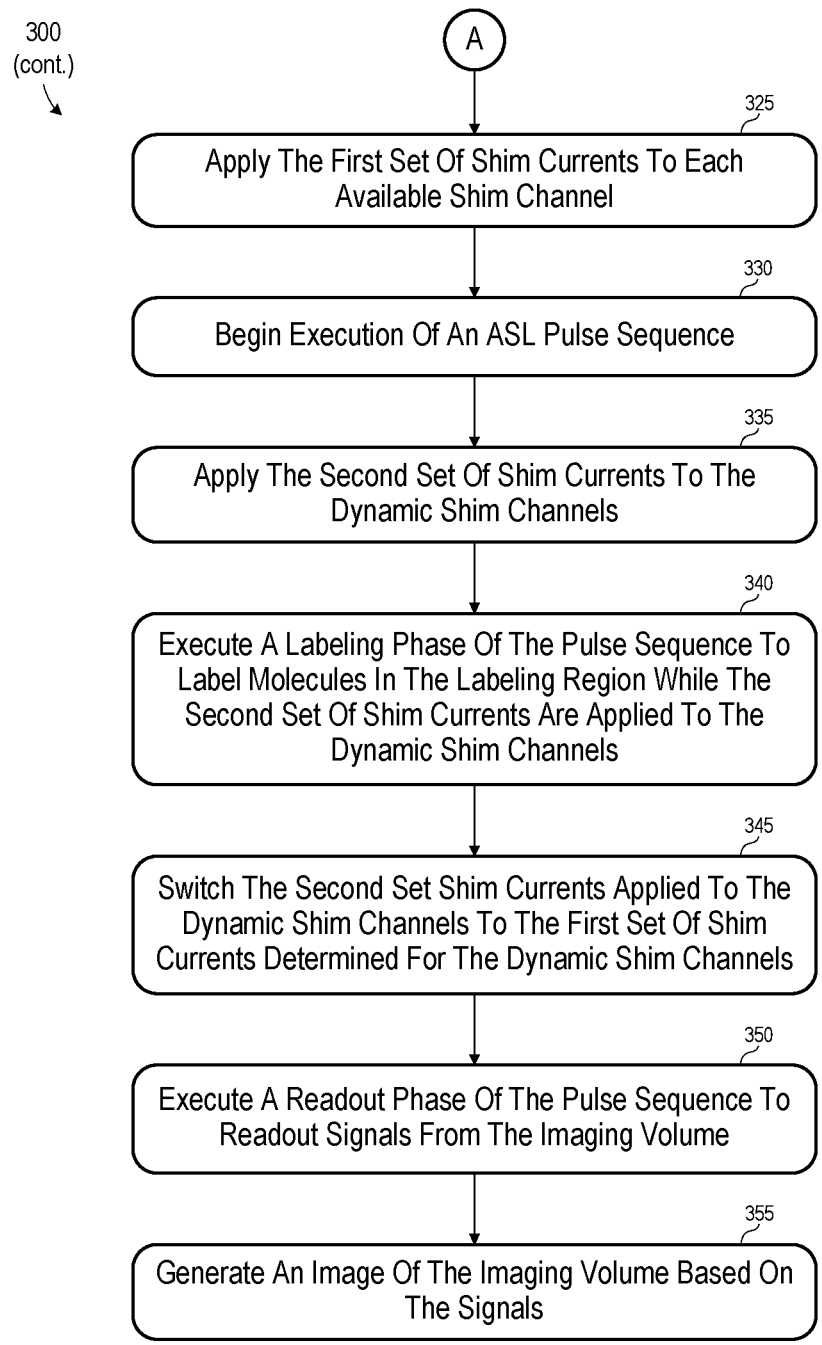

FIGS. 3A and 3B comprise a flow diagram of process 300 to dynamically shim a labeling region and an imaging volume according to some embodiments. Process 300 may be executed by various components of MR system 1, but embodiments are not limited thereto. In some embodiments, various hardware elements (e.g., one or more processing units) execute program code to perform process 300. The steps of process 300 need not be performed by a single device or system, nor temporally adjacent to one another.

Process 300 and all other processes mentioned herein may be embodied in program code read from one or more of non-transitory computer-readable media, such as a disk-based or solid-state hard drive, a DVD-ROM, a Flash drive, and a magnetic tape, and executed by one or more processing units (e.g., processors, processor cores, processor threads). In some embodiments, hard-wired circuitry may be used in place of, or in combination with, program code for implementation of processes according to some embodiments. Embodiments are therefore not limited to any specific combination of hardware and software.

Initially, an imaging volume and a labeling region are determined at 305. The location of imaging volume may be determined first, with the location of the labeling region selected to ensure that molecules labeled therein flow into the imaging volume shortly after such labeling.

305 may include operator selection of the imaging volume and the labeling region from a displayed scout image of the subject. The scout image may be generated by an MR scanner in which the subject is disposed. The pulse sequence used to acquire the k-space data of the scout image may be selected to generate a suitable scout image while requiring minimal acquisition time, such as a single-shot pulse sequence. The scout image may be acquired by another imaging modality, such as but not limited to computed tomography, positron emission tomography and single-photon emission computed tomography. If a non-MR modality is used, the scout image may be acquired so as to be registerable with the MR scanner to be used in subsequent steps of process 300.

Next, at 310, a set of available dynamic shim channels is determined from the set of all available shim channels. In one non-exhaustive example, a system includes a $0^{th}$-order shim channel consisting of frequency adjustment, a $1^{st}$-order linear shim channel implemented by gradient coils, superconducting shim coils which provide $2^{nd}$-order shimming and $3^{rd}$-order shimming, and a shim coil array placed near or on the subject. 310 may therefore consist of identifying the $0^{th}$-order shim channel, the $1^{st}$-order linear shim channel and the shim coil array as the available dynamic shim channels.

A first set of shim currents is determined at 315. Each of the first set of shim currents is to be applied to a respective one of the available shim channels during imaging of the imaging volume. Accordingly, the first set of shim currents is determined so as to reduce inhomogeneity and/or off-resonance in the $B_0$ field of the imaging volume when applied to the respective available shim channels. 315 may include mapping of the $B_0$ field in the imaging volume and determining the first set of shim currents to be applied to the available shim channels based on the mapping.

A second set of shim currents to be applied to respective ones of the dynamic during labeling of the labeling region is determined at 320. According to some embodiments, 320 includes mapping of the $B_0$ field in the labeling region. Based on the mapped $B_0$ field and under the assumption that the first set of shim currents are applied to respective ones of the non-dynamic shim channels during the labeling period, the second set of shim currents is determined so as to reduce inhomogeneity and/or off-resonance in the $B_0$ field of the labeling region.

While process 300 assumes the use of all available shim channels during both the labeling and readout phases, embodiments are not limited thereto. Less than all of the available shim channels, and less than all of the dynamic shim channels, may be used in either or both phases. Moreover, the shim current of the first set of shim currents determined for a dynamic shim channel at 315 may be equal to, less than or greater than the shim current of the second set of shim currents determined for the dynamic shim channel at 320.

At 325, the first set of shim currents are applied to respective ones of the available shim channels, to reduce inhomogeneity and/or off-resonance in the $B_0$ field of the imaging volume as mentioned above. Next, at 330, execution of an ASL pulse sequence commences as is known in the art. The pulse sequence may comprise a pCASL pulse sequence, but embodiments are not limited thereto.

Prior to a labeling phase of the pulse sequence, the shim currents applied to the dynamic shim channels are switched to the second set of shim currents at 335. In combination with the shim currents applied to the non-dynamic shim channels at 325, application of the second set of shim currents to the dynamic shim channels is intended to reduce inhomogeneity and/or off-resonance in the $B_0$ field of the labeling region. Accordingly, at 340, a labeling phase of the pulse sequence is executed to label molecules in the labeling region while the second set of shim currents are applied to the dynamic shim channels. For example, the labeling phase may consist of 750 Hanning-shaped 20° RF-pulses each lasting 0.5 msec applied over a 1.5 second period.

After execution of the labeling phase, the second set of shim currents applied to the dynamic shim channels are switched at 345 to the first set of shim currents determined for the dynamic shim channels. 345 occurs during a post-labeling period which is intended to allow the now-labeled molecules to flow from the labeling region to the imaging volume.

A readout phase of the pulse sequence is executed at 350 to readout signals from the imaging volume. During the readout phase, the first set of shim currents remain applied to respective ones of the available shim channels, so as to reduce inhomogeneity and/or off-resonance in the $B_0$ field of the imaging volume. As mentioned above, the readout phase may comprise an echo-planar imaging pulse sequence, a fast spin echo pulse sequence, a gradient-recalled echo pulse sequence, or any other suitable pulse sequence.

An image of the imaging volume is generated at 355 based on the signals acquired at 350. The image may comprise a two-dimensional or a three-dimensional image. The image may be displayed to an operator. As described above, a difference between the image and an image generated using the same readout pulse sequence and imaging shim channels/shim currents but without a preceding labeling phase may be calculated to generate a unitless perfusion-weighted image.

Figure 4A:
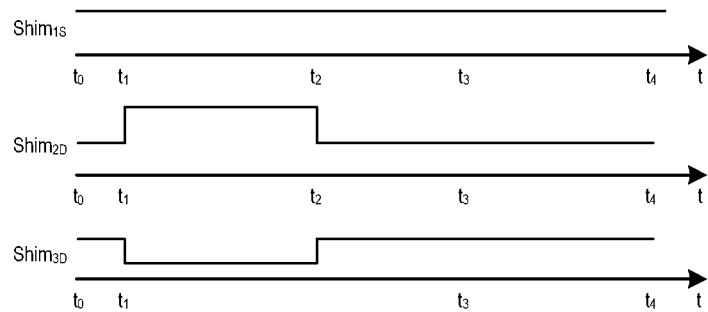
FIGS. 4A through 4C comprise timing diagrams of shim currents for various shim channels according to some embodiments.
Figure 4B:
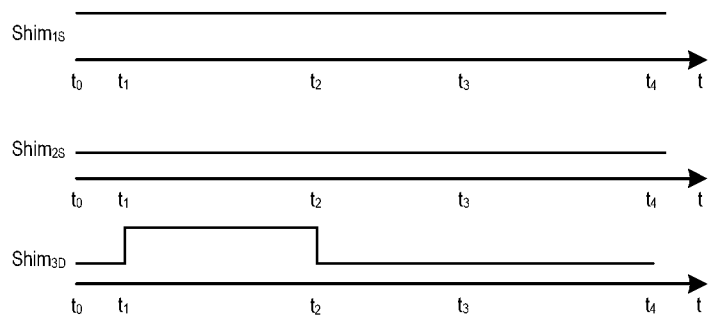
Figure 4C:
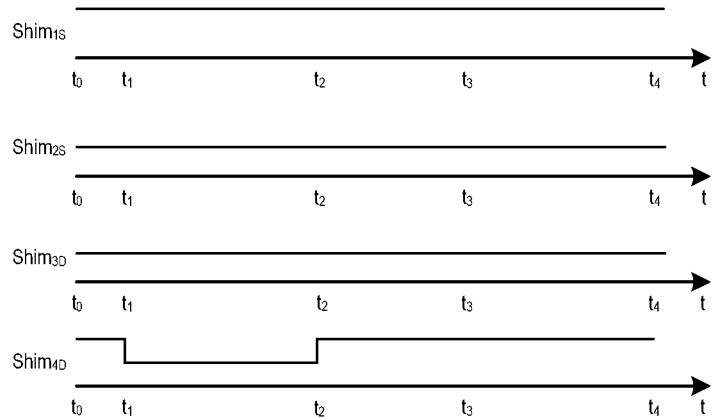

FIGS. 4A through 4C comprise timing diagrams of shim currents for various shim channels according to some embodiments. The illustrated time points $t_1$, $t_2$, $t_3$, $t_4$ correspond to the labeling and readout phases illustrated in FIG. 1. Embodiments are not limited to the scenarios illustrated in FIGS. 4A through 4C.

FIG. 4A illustrates the application of respective shim currents to one static shim channel (i.e., $Shim_{1S}$) and to two dynamic shim channels (i.e., $Shim_{2D}$ and $Shim_{3D}$) during the labeling phase. The shim currents applied to the two dynamic shim channels are switched from a first set of shim currents applied from $t_0$ to $t_1$ to a second set of shim currents applied during a labeling phase from $t_1$ to $t_2$ and back to the first set of shim currents which are applied during a readout phase from $t_3$ to $t_4$. The shim current applied to the static shim channel $Shim_{1S}$ remains the same throughout $t_0$ to $t_4$. As noted above, in some embodiments, the shim current applied to a dynamic shim channel may also remain the same throughout to to $t_4$.

FIG. 4B illustrates the application of two different respective shim currents to two static shim channels (i.e., $Shim_{1S}$ and $Shim_{2S}$) throughout the labeling and readout phases (i.e., from $t_1$ to $t_4$). A first shim current is applied to one dynamic shim channel (i.e., $Shim_{3D}$) prior to the labeling phase, is switched to a greater second shim current during a labeling phase from $t_1$ to $t_2$ and is switched back to the first shim current during a readout phase from $t_3$ to $t_4$.

FIG. 4C illustrates the application of two different respective shim currents to two static shim channels (i.e., $Shim_{1S}$ and $Shim_{2S}$) throughout the labeling and readout phases (i.e., from $t_1$ to $t_4$). A first shim current is applied to dynamic shim channel $Shim_{4D}$ prior to the labeling phase, is switched to a lower second shim current during a labeling phase from $t_1$ to $t_2$ and is switched back to the first shim current during a readout phase from $t_3$ to $t_4$. FIG. 4C also illustrates the application of a same shim current to dynamic shim channel $Shim_{3D}$ during the labeling phase and the readout phase, without any switching of the shim current applied thereto between the phases.

The foregoing diagrams represent logical architectures for describing processes according to some embodiments, and actual implementations may include more or different components arranged in other manners. Other topologies may be used in conjunction with other embodiments. Moreover, each component or device described herein may be implemented by any number of devices in communication via any number of other public and/or private networks. Two or more of such computing devices may be located remote from one another and may communicate with one another via any known manner of network(s) and/or a dedicated connection. Each component or device may comprise any number of hardware and/or software elements suitable to provide the functions described herein as well as any other functions. For example, any computing device used in an implementation of a system according to some embodiments may include a processor to execute program code such that the computing device operates as described herein.

Embodiments described herein are solely for the purpose of illustration. Those in the art will recognize other embodiments may be practiced with modifications and alterations to that described above.

What is claimed is:

1. A system comprising:
   a magnet system configured to generate a polarizing magnetic field about at least a portion of a subject;
   a gradient system to apply a gradient magnetic field to the polarizing magnetic field;
   a radio frequency (RF) system to apply an excitation field to the subject and to acquire magnetic resonance (MR) data from the subject;
   a display; and
   at least one processing unit to execute program code to:
      determine an imaging volume of the subject;
      determine a labeling region of the subject;
      determine a first one or more shim channels and respective first shim currents for the first one or more shim channels to label the labeling region and image the imaging volume;
      determine a second one or more shim channels, respective second shim currents for the second one or more shim channels to label the labeling region, and respective third shim currents for the second one or more shim channels to image the imaging volume, wherein the second shim current determined for one of the second shim channels is different from the third shim current determined for the one of the second shim channels;
      apply the first shim currents to respective ones of the first one or more shim channels and the second shim currents to respective ones of the second one or more shim channels;
      execute a labeling phase of a pulse sequence while the first shim currents are applied to respective ones of the first one or more shim channels and the second shim currents are applied to respective ones of the second one or more shim channels;
      apply the third shim currents to respective ones of the second one or more shim channels;
      execute a readout phase of the pulse sequence to readout signals from the imaging volume while the third shim currents are applied to respective ones of the second one or more shim channels and the first shim currents are applied to respective ones of the first one or more shim channels;
      generate an image of the imaging volume based on the signals; and
      display the image on the display.

2. A system according to claim 1, the at least one processing unit to execute program code to:
   identify the second one or more shim channels as dynamic shim channels of a plurality of available shim channels.

3. A system according to claim 2, wherein the plurality of available shim channels comprises only the first one or more shim channels and the second one or more shim channels.

4. A system according to claim 2, wherein the first one or more shim channels comprise one or more $n^{th}$-order (n>1) shim channels.

5. A system according to claim 1, wherein determination of the first one or more shim channels and respective first shim currents, and the second one or more shim channels and respective third shim currents, for imaging the imaging volume comprises mapping of the polarizing magnetic field within the imaging volume, and
   wherein determination of the first one or more shim channels and respective first shim currents, and the second one or more shim channels and respective second shim currents, for labeling the labeling region comprises mapping of the polarizing magnetic field within the labeling region.

6. A system according to claim 1, wherein the pulse sequence is an arterial spin labeling pulse sequence.

7. A system according to claim 6, wherein the pulse sequence is a pseudo-continuous arterial spin labeling pulse sequence.

8. A method comprising:
determining an imaging volume of a subject;
determining a labeling region of the subject;
determining a first one or more shim channels and respective first shim currents for the first one or more shim channels for reducing magnetic field off-resonance in the labeling region and for reducing magnetic field off-resonance in the imaging volume;
determining a second one or more shim channels, respective second shim currents for the second one or more shim channels for reducing magnetic field off-resonance in the labeling region, and respective third shim currents for the second one or more shim channels for reducing magnetic field off-resonance in the imaging volume;
applying the first shim currents to respective ones of the first one or more shim channels and the second shim currents to respective ones of the second one or more shim channels;
executing a labeling phase of a pulse sequence while the first shim currents are applied to respective ones of the first one or more shim channels and the second shim currents are applied to respective ones of the second one or more shim channels;
applying the third shim currents to respective ones of the second one or more shim channels;
executing a readout phase of the pulse sequence to readout signals from the imaging volume while the third shim currents are applied to respective ones of the second one or more shim channels and the first shim currents are applied to respective ones of the first one or more shim channels;
generating an image of the imaging volume based on the signals; and
displaying the image on a display.

9. A method according to claim 8, further comprising:
identifying the second one or more shim channels as dynamic shim channels of a plurality of available shim channels.

10. A method according to claim 9, wherein the plurality of available shim channels comprises only the first one or more shim channels and the second one or more shim channels.

11. A method according to claim 9, wherein the first one or more shim channels comprise one or more $n^{th}$-order (n>1) shim channels.

12. A method according to claim 8, wherein determining the first one or more shim channels and respective first shim currents, and the second one or more shim channels and respective third shim currents, for imaging the imaging volume comprises mapping of the polarizing magnetic field within the imaging volume, and
wherein determining the first one or more shim channels and respective first shim currents, and the second one or more shim channels and respective second shim currents, for labeling the labeling region comprises mapping of the polarizing magnetic field within the labeling region.

13. A method according to claim 8, wherein the pulse sequence is an arterial spin labeling pulse sequence.

14. A method according to claim 13, wherein the pulse sequence is a pseudo-continuous arterial spin labeling pulse sequence.

15. A system comprising:
a memory storing program code; and
one or more processing units to execute the program code to:
determine an imaging volume of a subject;
determine a labeling region of the subject;
determine a first one or more shim channels and respective first shim currents for the first one or more shim channels for reducing magnetic field off-resonance in the labeling region and for reducing magnetic field off-resonance in the imaging volume;
determine a second one or more shim channels, respective second shim currents for the second one or more shim channels for reducing magnetic field off-resonance in the labeling region, and respective third shim currents for the second one or more shim channels for reducing magnetic field off-resonance in the imaging volume;
apply the first shim currents to respective ones of the first one or more shim channels and the second shim currents to respective ones of the second one or more shim channels;
execute a labeling phase of a pulse sequence while the first shim currents are applied to respective ones of the first one or more shim channels and the second shim currents are applied to respective ones of the second one or more shim channels;
apply the third shim currents to respective ones of the second one or more shim channels;
execute a readout phase of the pulse sequence to readout signals from the imaging volume while the third shim currents are applied to respective ones of the second one or more shim channels and the first shim currents are applied to respective ones of the first one or more shim channels;
generate an image of the imaging volume based on the signals; and
display the image on a display.

16. A system according to claim 15, the one or more processing units to execute the program code to:
identify the second one or more shim channels as dynamic shim channels of a plurality of available shim channels.

17. A system according to claim 15, wherein the plurality of available shim channels comprises only the first one or more shim channels and the second one or more shim channels.

18. A system according to claim 15, wherein determination of the first one or more shim channels and respective first shim currents, and the second one or more shim channels and respective third shim currents, for imaging the imaging volume comprises mapping of the polarizing magnetic field within the imaging volume, and
wherein determination of the first one or more shim channels and respective first shim currents, and the second one or more shim channels and respective second shim currents, for labeling the labeling region comprises mapping of the polarizing magnetic field within the labeling region.

19. A system according to claim 15, wherein the pulse sequence is an arterial spin labeling pulse sequence.

20. A system according to claim 19, wherein the pulse sequence is a pseudo-continuous arterial spin labeling pulse sequence.

\* \* \* \* \*